Figure 1:
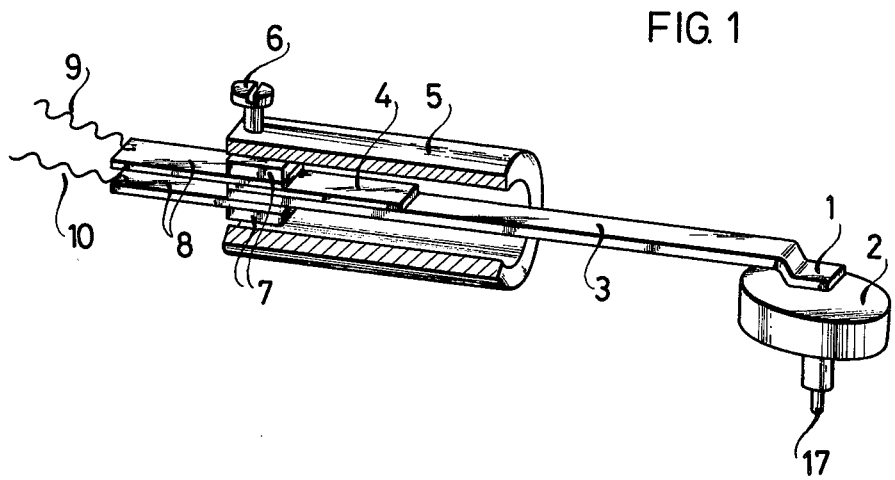

United States Patent [19]
Besocke

[11] 4,100,442
[45] Jul. 11, 1978

[54] ELECTRICALLY DRIVEN OSCILLATING CAPACITOR DEVICE

[75] Inventor: Karl Heinz Besocke, Julich, Germany

[73] Assignee: Kernforschungsanlage Jülich Gesellschaft mit beschränkter Haftung, Jülich, Germany

[21] Appl. No.: 779,837

[22] Filed: Mar. 21, 1977

[30] Foreign Application Priority Data

Mar. 30, 1976 [DE] Fed. Rep. of Germany ....... 2613528

[51] Int. Cl.² .......................................... H01L 41/10
[52] U.S. Cl. .................................... 310/317; 310/321; 361/289
[58] Field of Search ............... 200/181; 310/317, 330, 310/331, 321, 332, 328; 361/289

[56] References Cited

U.S. PATENT DOCUMENTS

| | | | |
|---|---|---|---|
| 1,900,038 | 3/1933 | Bower | 310/330 X |
| 2,368,643 | 2/1945 | Crosby | 310/330 X |
| 2,682,623 | 6/1954 | Woodyard et al. | 310/328 X |
| 2,937,562 | 5/1960 | Robillard | 310/317 X |
| 2,983,902 | 5/1961 | Philipps | 310/331 X |
| 3,117,440 | 1/1964 | Wilner | 310/328 X |
| 3,336,529 | 8/1967 | Tygart | 310/321 X |
| 3,501,745 | 3/1970 | Beckman | 310/321 X |
| 3,646,413 | 2/1972 | Oomen | 310/331 X |

*Primary Examiner*—Mark O. Budd
*Attorney, Agent, or Firm*—Flynn & Frishauf

[57] ABSTRACT

A spring member is resin bonded to a piezoelectric material body at one end and at the other end carries the oscillating electrode of a Kelvin probe capacitor used for electron work function measurement under vacuum. The piezoelectric material body can be either a piezoelectric crystal or a piezoceramic. An alternating voltage causes it to vibrate the spring member at a resonant frequency, so that a still greater amplitude of vibration is produced at the electrode. A superimposed d-c voltage is applied to the piezoelectric material body to set the average spacing between the movable reference electrode and the fixed sample electrode. A polyurethane-based resin provides vacuum-proof bonding. The piezoelectric material body and spring are mounted in a tube providing electrostatic shielding. The electrical circuits for a-c excitation and for synchronous detection of displacement currents resulting from differences in contact potential of the respective electrode materials are all located outside the vacuum chamber.

9 Claims, 2 Drawing Figures

U.S. Patent    July 11, 1978    Sheet 1 of 2    4,100,442

ELECTRICALLY DRIVEN OSCILLATING CAPACITOR DEVICE

This invention relates to an oscillating capacitor device for a dynamic electron electrometer having an electromechanical drive for the oscillating electrode.

Oscillating capacitors are used particularly for the determination of the work function that determines the energy necessary for an electron to be drawn or emitted from the surface of a material. The work function is sometimes referred to as the electron affinity of the material. The electron work function of the surfaces of electrical conductors or semi-conductors is of particular interest. The determination of the electron work function is of significance for the surface properties of materials. Photoelectric methods, thermionic methods and contact potential difference measurement methods are known for measuring the work function. The last-mentioned method is preferably used since it is one in which the measuring process does not influence the surface under investigation. The measurements are made in spaces filled with gas of the highest purity or in very high vacuum, i.e. at a pressure less than $10^{-10}$ torr.

Oscillating capacitors for determining work functions have become known as so-called "Kelvin probes". When a Kelvin probe is used, the contact potential between boundary surfaces of two materials with different electron work functions is measured (cf. Review of Scientific Instruments, 1970, Vol. 41, p. 258). The oscillating electrode of the probe is in most cases used as the reference electrode. It consists of a material that does not change its electron work function during the measuring period. The test sample for the surface of which the work function is to be determined constitutes the counterelectrode. The movement of the reference electrode with respect to the test sample causes the capacitance of the capacitor formed by the two electrodes to vary. When there is a difference in work function between the reference electrode and the test sample, a displacement current flows that is proportional to the contact potential difference. The oscillating movement of the movable electrode in a Kelvin probe is generated by mechanical or electromechanical method. For that purpose it is necessary to decouple the electrical exciting system and the generated signal to be measured from each other, in order to maintain as high as possible the sensitivity of the Kelvin probe. Measurement in measuring chambers filled with gas of the highest purity or maintained under very high vacuum generally makes it necessary to provide the electrical exciting system outside of the chamber. This requirement has been a great disadvantage of electromechanical drive because of the mechanical coupling between the electrical exciting system on the outside of the chamber and the vibrating electrode inside of the chamber. Difficulties also beset the adjustment between the vibrating electrode and the counter-electrode for setting the average spacing. The exact determination of the work function by the Kelvin method has therefore been possible only with considerable technical complication and expense (cf. Journal of Physics, E: Scientific Instruments, 1970, Vol. 3, pp. 477 ff).

It is an object of the present invention to provide an oscillating capacitor device of high sensitivity in which the oscillating electrode is movable by an electromechanical exciting system that can be installed inside the measuring chamber with the smallest possible space requirement. At the same time it is an object to reduce the technical complication and expense of the determination of electron work functions by means of Kelvin probes.

SUMMARY OF THE INVENTION

Briefly, a spring member, preferably a leaf spring, is mounted so as to be excitable at one of its frequencies of resonance by a body of piezoelectric material, preferably by bonding one end of it to the piezoelectric material body with a synthetic resin, and the movable electrode is provided at a location of or on the spring member distant from the piezoceramic or other piezoelectric body. An alternating voltage is applied to the piezoelectric material body so as to set it in vibration at one of the aforsaid resonance frequencies and at the same time a superposed d-c voltage is also applied to the piezoelectric material so as to set the average spacing between the movable electrode and a fixed electrode which, as usual, generally is a test sample.

Piezoelectric vibrating drives for Kelvin probes are known, as disclosed in the Journal of Physics reference cited above, at p. 479. That disclosure, however, does not show a suitable drive arrangement between the piezoelectric material and the oscillating electrode. The piezoelectric drive of the device of the present invention, on the other hand, requires only little electric energy, so that the exciting field of the crystal provides only negligibly small disturbance of the measurement signal produced by the Kelvin probe. In the present invention piezoelectric material and spring member provide an exciting system for the oscillating electrode having extremely small space requirements. This excitation system lends itself readily to installation in the measuring chamber itself, so that all that needs to be run through the walls of the measuring chamber are the electrical conductors for the exciting voltage of the crystal and the electrical conductors for bringing out the measurement signal. The spring member and thereby the movable electrode of the capacitor are put into oscillation in the known way by adjusting the excitation frequency to the fundamental resonance frequency or an overtone resonance frequency of the spring member or by using a self-maintaining oscillator circuit.

A further advantage of the invention lies in the superposition of a d-c voltage component on the alternating electric field that excites the piezoelectric material. Under the application of a constant d-c voltage the piezoelectric material body is deformed and provides a bias offset to the spring member and its electrode. The deformation determines the average spacing between the oscillating electrode and the counter-electrode. Preferably the d-c component is adjustable, so that a ready possibility of adjusting the position of the reference electrode relative to the test sample is provided for measurement of the work function by means of an Kelvin probe device of the present invention.

In order to increase the sensitivity of the Kelvin probe device, in a further elaboration of the invention, electrostatic shielding is provided for the piezoelectric material. In order to provide bonding between the piezoelectric material and the spring member that will not deteriorate even at ultrahigh (UHV) vacuum, the piezoelectric material and the spring element are preferably bonded by means of a two-component resin having a polyurethane base (cf. Vakuumtechnik, 1973, Heft b 3, p. 93 ff). These resins harden with moderate shrinking even at room temperature and enable an intimate bonding to be obtained between piezoelectric material and spring member after applying a uniform film of resin. It is advantageous to provide the spring member in the form of a leaf spring, since in this way, for a comparable amount of deformation of the piezoelectric material body, an increased amplitude of oscillation of the vibrating electrode can be obtained.

Not only metal, but also electrically insulating materials are usable as the material for the spring member. In order to obtain the highest possible excitation frequencies, it is desirable in the selection of the material to prefer those with high modulus of elasticity and low density. Materials such as tungsten, titanium, molybdenum, beryllium are particularly suitable, as is also mica.

Figure 2:
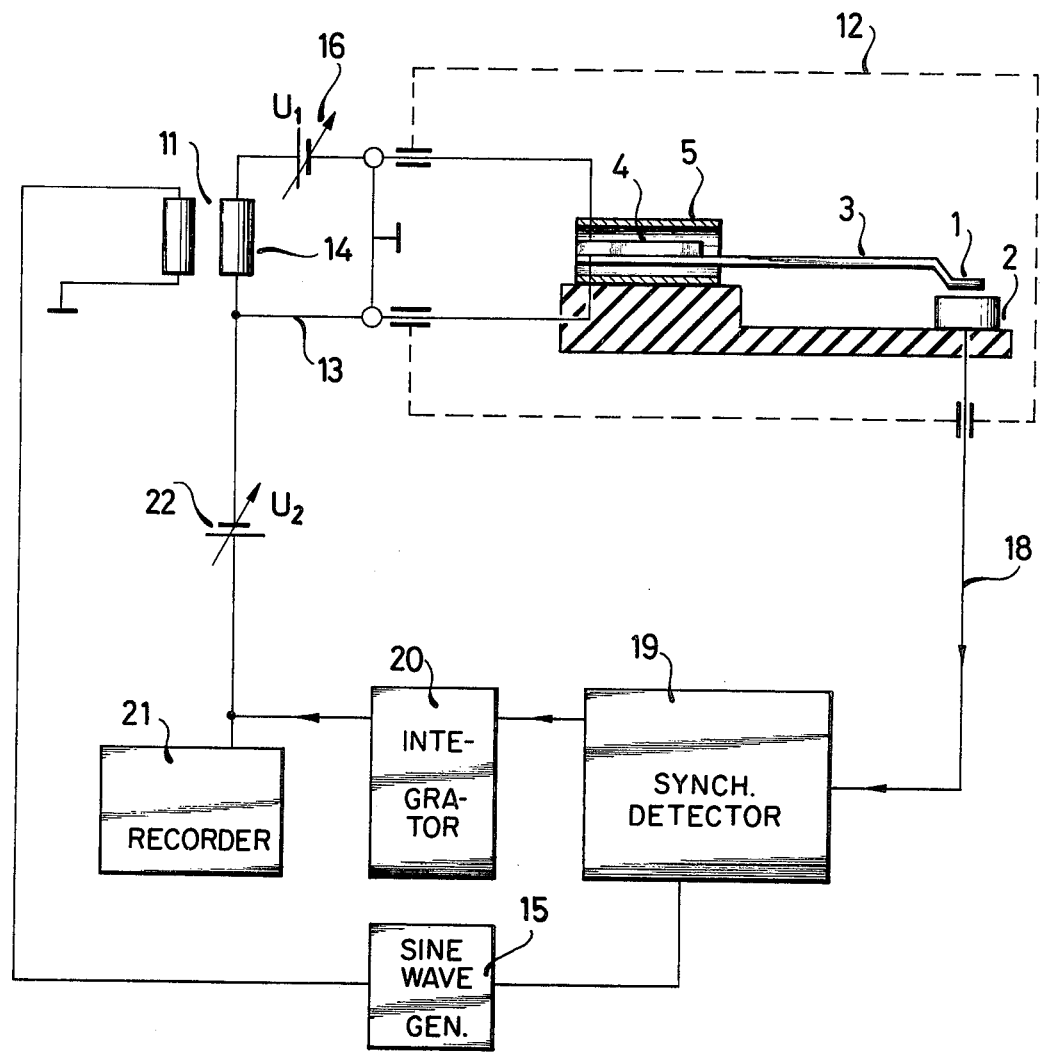

The invention is further described by way of example with reference to the accompanying drawings, in which:

FIG. 1 is a perspective view, partly cut away, of an electrically driven oscillating capacitor for measuring electron work function, and FIG. 2 is a block diagram of a circuit for measurement of work function with an oscillating capacitor of the kind of FIG. 1.

As the drawings show, the oscillating capacitor consists of a vibrating electrode 1 and and a fixed counter-electrode 2. For operation as a Kelvin probe, the oscillating electrode 1 of the capacitor is provided as the reference electrode. It consists of a material of which the work function does not change during the intended measuring period, for example gold or $SnO_2$. The test sample constitutes the counter-electrode 2. The oscillating electrode 1 is affixed to a spring member 3 that is excited, as a leaf spring, into transversal vibrations at its other end by a piezoelectric crystal 4. Instead of a leaf spring other spring members are usable, particularly longitudinal mode vibrators. The leaf spring member 3 shown in the drawing is made of molybdenum.

The piezoelectric body 4 bonded to the spring member 3, a wafer of piezoelectric ceramic of a thickness of 0.1mm, is coated on both sides with a metal layer and these are connected to an alternating voltage source for exciting the piezoelectric body. Piezoelectric ceramic materials capable of withstanding temperatures over a sufficiently wide range and also withstanding extremely high vacuum are to be used, for example, wafers of piezoelectric ceramic formed of lead zirconate and titanate with 0.5% by weight of neodymium as an additive. Such piezoelectric ceramic wafers or plates are commercially available under the designation PTZ-H-42. The piezoelectric ceramic of FIG. 1 was provided with gold contact layers. The piezoelectric body is deformed mechanically when an electric voltage is applied and its movement is transmitted to the spring member and thereby to the electrode 1 affixed to the spring member so that the latter changes its spacing from the counter-electrode, i.e. from the test sample.

Metallic shielding 5 surrounds the piezoelectric body 4. The sensitivity of the oscillating capacitor is thereby increased. The shielding 5 at the same time provides the holding structure for the vibrating arm that is composed of the piezoelectric material body 4, the spring member 3 and the electrode 1. This vibrating arm is secured between two insulating pieces 7 and electrical conductors 8 within the shielding 5 by means of a clamping screw 6. The electrical conductors 8 are connected to leads 9 and 10 that in turn are connected to an alternating voltage source 11. The leads 9 and 10 and likewise sheathed with electrical shielding not shown in the drawing.

Piezoelectric material 4 is bonded to the spring member 3 by means of a hardenable polyurethane-base resin that is already known as a vacuum-sealing medium. In the illustrative example a two component resin available under the commercial name "Desmodur-Desmophen-Lack" is used which is free-flowing and wets the surfaces readily. The vibrating arm has the following dimensions.

Leaf spring — length 26 mm, widths 1.5 mm and thickness 0.1 mm;
Electrode contact surface — 2 × 2.55 $mm^2$;
Piezoelectric body — length 10 mm, width 1.5 mm and thickness 0.1 mm;
Shielding 5 — diameter about 5 mm, length 15 mm.

As shown in FIG. 2, for excitation of the piezoelectric material 4 the leads 9 and 10 coming out of the measurement chamber 12 are connected in a circuit 13 with a secondary winding 14 of a transformer of which the primary winding is fed by a sine wave generator 15 in order to serve as the alternating voltage source 11. In the circuit 13 there is additionally a voltage source 16 for insertion of a constant d-c voltage superimposed on the alternating voltage, by which the average spacing between the oscillating electrode 1 and the counter-electrode 2 can be adjusted.

The measurement signal is brought out of the measuring chamber by a conductor 17 (FIG. 1) that is further continued by a connecting line 18 to a synchronous detector circuit 19 which is provided with a synchronizing connection to the sine wave generator 15. As intergrator 20 responds to automatic null balancing provided in detector 19 and thereby provides an indication of the change of work function to be measured that is directly recordable in a recording device 21. In the circuit loop from the connection 18 around to the circuit 13 there is also inserted another d-c voltage source 22 that serves to simulate a work function change.

Before the assembly of the oscillating capacitor device, the piezoelectric crystal destined to serve for exciting the oscillating electrode is polarized, for example by means of a pulse of d-c voltage exceeding 100 volts. The bonded oscillating arm for the capacitor is, moreover, subjected to ultrasonic treatment and dried for 3 hours at 200° C for removal of the ultrasonic medium. After installation of the vibrating arm in the measuring chamber the entire system in the chamber is further heated at 200° C for 24 hours under vacuum. After this treatment no impurities of any kind were observable at an extreme vacuum of $4 \times 10^{-11}$ torr. Measurements of change of work function were carried with excitation of the spring member at its fundamental frequency and at its second overtone. For the molybdenum leaf spring used for this purpose in the illustrated example, with the dimensions given further above, there were found a fundamental resonance frequency of 145 hertz and a second overtone at 750 hertz.

For determination of work function in this embodiment of the oscillating capacitor device, a vibration amplitude of 0.2 mm was set. The alternating voltage necessary to excite the piezoelectric crystal for this vibration amounts to only 0.3 volts in the case of the fundamental oscillation and 1.3 volts in the case of the second overtone and the necessary currents were below one microampere. Under these operating conditions the stray fields produced by the exciting field are very small.

For setting the average spacing between the electrode 1 and counter-electrode 2 a d-c voltage in the range ± 70 volts is available from the voltage source 16, by the variation of which the average spacing between movable electrode and counter-electrode can be varied by up to ± 0.5 mm. The measurement accuracy of the oscillating capacitor device can be found by simulation of a work function change by use of the voltage source 22. For a time constant (of the integrator) less than 10 seconds a resolution of 0.1 millivolt was obtained.

The drive system of the oscillating capacitor according to the present invention by means of a body of piezoelectric material and a spring member lends itself simply to variations and modifications, for example, provision of an electronic self-excitation circuit for the vibrating arm of the capacitor consisting of piezoelectric crystal, spring element and electrode. The d-c voltage source 16 is also replaceable by an electronic regulating circuit, for example, by which a predetermined average spacing between the vibrating electrode and the test sample can be automatically reinstated after disturbance such as may be occasioned, for example, by replacement or manipulation of the test sample.

I claim:

1. An electrically driven Kelvin probe apparatus for operation as a dynamic electron electrometer or as a contact potential meter comprising, in combination:
   a body of piezoelectric material (4);
   a spring member (3) mounted so as to be excitable at a frequency of resonance thereof by piezoelectric vibration of said piezoelectric material body and extending away from said piezoelectric material body and providing a movable capacitor electrode (1) at or on a portion of said spring member at a distance from said piezoelectric material body;
   means for holding a fixed capacitor electrode (2), of a material to be observed, in spaced proximity to said movable capacitor electrode (1) provided by or on said spring member (3);
   a vacuum enclosure, capable of being evacuated to a high vacuum, enclosing said body of piezoelectric material, said spring member and said holding means as well as any electrode (2) held by said holding means;
   means (7–11; 15) for applying an alternating voltage of a frequency of resonance of said spring member through said enclosure to said piezoelectric material body so as to cause said piezoelectric material body to vibrate said spring member at said frequency, and
   means (16) for superimposing a d-c voltage component on said applied alternating voltage.

2. A Kelvin probe apparatus as defined in claim 1 in which means are provided for varying said superimposed d-c voltage component.

3. A Kelvin probe apparatus as defined in claim 1 comprising also means (5) for electrostatically shielding said piezoelectric material body (4).

4. A Kelvin probe apparatus as defined in claim 1 in which said spring member (3) is bonded to said piezoelectric material body (4) by means of a two-component resin having polyurethane base.

5. A Kelvin probe apparatus as defined in claim 1 in which said spring member (3) is in the form of a leaf spring.

6. A Kelvin probe apparatus as defined in claim 1 in which said spring member is made of a low density material having a high modulus of elasticity.

7. A Kelvin probe apparatus as defined in claim 6 in which said spring member (3) is a leaf spring made of a material selected from the group consisting of tungsten, titanium, molybdenum, beryllium steel and mica.

8. An electrically driven Kelvin probe apparatus for operation as a dynamic electron electrometer or as a contact potential meter, comprising in combination:
   a body of piezoelectric material (4);
   a spring member (3) mounted so as to be excitable at a frequency of resonance thereof by piezoelectric vibration of said piezoelectric material body and extending away from said piezoelectric material body and providing a movable capacitor electrode (1) at or on a portion of said spring member at a distance from said piezoelectric material body
   means for holding a fixed capacitor electrode (2), of a material to be observed, in spaced proximity to said movable capacitor electrode (1) provided by or on said spring member (3);
   a vacuum enclosure, capable of being evacuated to a high vacuum, enclosing said body of piezoelectric material, said spring member and said holding means as well as any electrode (2) held in said holding means,
   means (7–11; 15) for applying an alternating voltage of a frequency of resonance of said spring member through said enclosure to said piezoelectric material body so as to cause said piezoelectric material body to vibrate said spring member at said frequency;
   means (16) for superimposing a d-c voltage component on said applied alternating voltage, and
   a synchronous detector connecting to said holding means for contacting said electrode (2) thereby and also connecting to said alternating voltage applying means, and
   means for indicating a detected voltage characteristic of the pair of materials of said respective movable and fixed electrodes.

9. A Kelvin probe apparatus as defined in claim 8 comprising also means for inserting an adjustable d-c voltage in a manner capable of simulating a change in the work function of the material of said fixed electrode and thereby testing the sensitivity of the apparatus.

* * * * *